(12) United States Patent
Lee et al.

(10) Patent No.: US 9,724,336 B2
(45) Date of Patent: Aug. 8, 2017

(54) PHARMACEUTICAL COMPOSITION FOR PREVENTING OR TREATING HYPERLIPIDEMIA

(71) Applicant: DAEWOONG PHARMACEUTICAL CO., LTD., Gyeonggi-do (KR)

(72) Inventors: Jong-Wook Lee, Gyeonggi-do (KR); Sang-Ho Lee, Gyeonggi-do (KR); Taek-Joo Lim, Seoul (KR); Eun-Ji Koh, Gyeonggi-do (KR)

(73) Assignee: DAEWOONG PHARMACEUTICAL CO., LTD., Gyeonggi-do (KR)

( * ) Notice: Subject to any disclaimer, the term of this patent is extended or adjusted under 35 U.S.C. 154(b) by 0 days.

(21) Appl. No.: 14/361,371

(22) PCT Filed: Nov. 28, 2012

(86) PCT No.: PCT/KR2012/010170
§ 371 (c)(1),
(2) Date: May 29, 2014

(87) PCT Pub. No.: WO2013/081372
PCT Pub. Date: Jun. 6, 2013

(65) Prior Publication Data
US 2014/0336229 A1    Nov. 13, 2014

(30) Foreign Application Priority Data
Nov. 30, 2011 (KR) .......................... 10-2011-0126431

(51) Int. Cl.
| | | |
|---|---|---|
| *A61K 31/421* | (2006.01) | |
| *A61K 31/4178* | (2006.01) | |
| *A61K 31/4184* | (2006.01) | |
| *C07D 263/22* | (2006.01) | |
| *A61K 31/216* | (2006.01) | |
| *A61K 31/4422* | (2006.01) | |
| *A61K 45/06* | (2006.01) | |
| *A61K 31/41* | (2006.01) | |

(52) U.S. Cl.
CPC .......... *A61K 31/421* (2013.01); *A61K 31/216* (2013.01); *A61K 31/41* (2013.01); *A61K 31/4178* (2013.01); *A61K 31/4184* (2013.01); *A61K 31/4422* (2013.01); *A61K 45/06* (2013.01); *C07D 263/22* (2013.01)

(58) Field of Classification Search
None
See application file for complete search history.

(56) References Cited

U.S. PATENT DOCUMENTS

| | | |
|---|---|---|
| 2008/0242711 A1 | 10/2008 | Tung |
| 2009/0137548 A1 | 5/2009 | Ali et al. |
| 2010/0099716 A1 | 4/2010 | Ali et al. |
| 2011/0165239 A1 | 7/2011 | Alani et al. |
| 2011/0218177 A1 | 9/2011 | Mills et al. |

FOREIGN PATENT DOCUMENTS

WO    2006/014357 A1    2/2006

OTHER PUBLICATIONS

Krishna et al., Lancet, 2007, vol. 370, pp. 1907-1914.*
Mason, Vascular Health and Risk Management, Jun. 2011, vol. 7, pp. 405-416.*
Okada et al., Hypertension Res., 2004, vol. 27, No. 4, pp. 293-299.*
Foucquier et al., Pharmacology Research & Perspectives, 2015, vol. 3, No. 3, e00149.*
Potts et al., Virology, 1993, vol. 197, No. 1, pp. 415-419.*
Meletiadis et al., Int.J.Antimicrob.Ag., 2006, vol. 28, pp. 439-449.*
Chapman et al., Eur. Heart J., 2010, vol. 31, No. 2, pp. 149-164.*
Cullen, "Evidence That Triglycerides are an Independent Coronary Heart Disease Risk Factor", Am J. Cardiol, vol. 86, pp. 943-949, (2000).
Le et al., "The Role of hypertriglyceridemia in altherosclerosis", Current Atherosclerosis Reports, vol. 9, Iss. 2, pp. 110-115, (2007).
Stalenhoef et al., "Association of fasting and nonfasting serum triglycerides with cardiovascular disease and the role of remnant-like lipoproteins and small dense LDL", Current Opinion in Lipidology, vol. 19, pp. 355-361, (2008).
The Communication pursuant to Article 94(3) EPC, for EP Application No. 12 852 736.3, mailed Feb. 5, 2016, five pages.
Chapman et al., "Cholesteryl ester transfer protein: at the heart of the action of lipid-modulating therapy with statins, fibrates, niacin, and cholesteryl ester transfer protein inhibitors", European Heart Journal (Online), Oxford University Press, GB, US, NL, vol. 31, No. 2, Jan. 1, 2010 (Jan. 1, 2010), pp. 149-164, XP002638290.
Kyvelou et al., "Effects of antihypertensive treatment with anglotensin II receptor blockers on lipid profile: an open multi-drug comparison trial", Hellenic journal of cardiology: HJC=Hellenike kardiologike epitheorese, vol. 47, No. 1, Jan. 1, 2006 (Jan. 1, 2006), pp. 21-28, XP055173036, Greece.

* cited by examiner

*Primary Examiner* — Jeffrey S Lundgren
*Assistant Examiner* — Stephanie Springer
(74) *Attorney, Agent, or Firm* — Vorys, Sater, Seymour & Pease LLP; Mih Suhn Koh

(57) ABSTRACT

Provided is a pharmaceutical composition for preventing or treating hyperlipidemia comprising (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one or its pharmaceutically acceptable salt; and an angiotensin II receptor blocker as active ingredients.

2 Claims, No Drawings

PHARMACEUTICAL COMPOSITION FOR PREVENTING OR TREATING HYPERLIPIDEMIA

TECHNICAL FIELD

The present invention relates to a pharmaceutical composition for preventing or treating hyperlipidemia. More specifically, the present invention relates to a pharmaceutical composition for preventing or treating hyperlipidemia comprising (4S,5R)-5-[3,5-bis(trifluoromethyl)phenyl]-3-({2-[4-fluoro-2-methoxy-5-(propan-2-yl) phenyl]-5-(trifluoromethyl)phenyl}methyl)-4-methyl-1,3-oxazolidin-2-one or its pharmaceutically acceptable salt; and an angiotensin II receptor blocker as active ingredients.

BACKGROUND ART

Hyperlipidemia involves abnormally elevated levels of any or all lipids and/or lipoproteins in the blood. Hyperlipidemias may be classified according to which types of lipids are elevated, that is hypercholesterolemia, hypertriglyceridemia or both in combined hyperlipidemia. Triglycerides are known as one of the independent risk factors of atherosclerosis. Although the relevancy between hypertriglyceridemia and cardiovascular diseases such as atherosclerosis is not still clear, it has been known that hypertriglyceridemia increases the risk of atherosclerosis (Cullen P. Evidence that triglycerides are an independent coronary heart disease risk factor. *Am J Cardiol* 2000; 86:943-9; Le N A, Walter M F. The role of hypertriglyceridemia in atherosclerosis. *Curr Atheroscler Rep* 2007; 9:110-5; Stalenhoef A F, de Graaf J. Association of fasting and nonfasting serum triglycerides with cardiovascular disease and the role of remnant-like lipoproteins and small dense LDL. *Curr Opin Lipidol* 2008; 19:355-61). And also, it has been reported that pancreatitis occurs in people whose triglyceride levels are above 1000 mg/dl or 12 mmol/l.

Meanwhile, the compound of the following formula 1, whose chemical name is (4S,5R)-5-[3,5-bis(trifluoromethyl)phenyl]-3-({2-[4-fluoro-2-methoxy-5-(propan-2-yl) phenyl]-5-(trifluoromethyl)phenyl}methyl)-4-methyl-1,3-oxazolidin-2-one, has a selective cholesterol ester transfer protein (CETP) inhibiting activity. The compound is being developed as a drug for preventing or treating atherosclerosis (International Patent Publication No. WO 2006/014357).

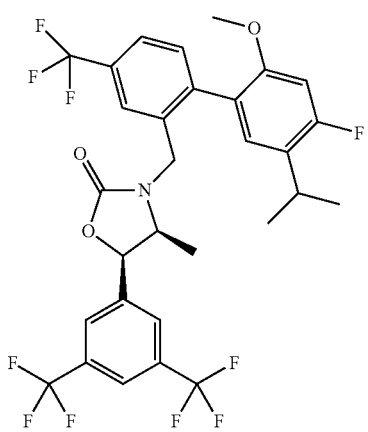

<Formula 1>

DISCLOSURE OF INVENTION

Technical Problem

The present inventors performed various researches for developing a drug or a drug-combination capable of providing effective therapeutic efficacy against hyperlipidemia. Surprisingly, the present inventors found that co-administration of the compound of Formula 1 and an angiotensin II receptor blocker can remarkably inhibit the concentration of triglycerides in the blood; and increase HDL cholesterols in the blood, in comparison with the administration of the compound of Formula 1 alone.

Therefore, it is an object of the present invention to provide a pharmaceutical composition for preventing or treating hyperlipidemia comprising the compound of Formula 1 and an angiotensin II receptor blocker as active ingredients.

Solution to Problem

In accordance with an aspect of the present invention, there is provided a pharmaceutical composition for preventing or treating hyperlipidemia comprising a compound of Formula 1 or its pharmaceutically acceptable salt; and an angiotensin II receptor blocker as active ingredients:

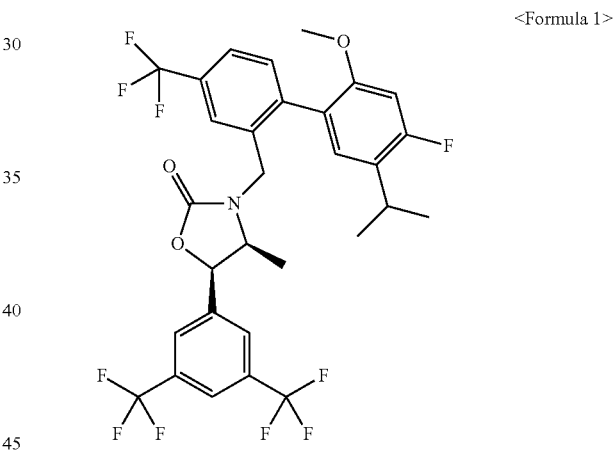

<Formula 1>

In the pharmaceutical composition of the present invention, the angiotensin II receptor blocker may be selected from the group consisting of olmesartan or its salt, olmesartan medoxomil or its salt, telmisartan or its salt, losartan or its salt, and valsartan or its salt. Preferably, the angiotensin II receptor blocker may be olmesartan medoxomil or its salt.

In an embodiment of the present invention, the hyperlipidemia may be hypertriglyceridemia or hypertriglyceridemia-associated disease. The hypertriglyceridemia-associated disease includes atherosclerosis or pancreatitis. In another embodiment of the present invention, the hyperlipidemia may be hypercholesterolemia. In still another embodiment of the present invention, the hyperlipidemia may be combined hyperlipidemia.

The pharmaceutical composition of the present invention may be formulated into a dosage form for oral administration. The dosage form for oral administration may comprise the compound of Formula 1 or its pharmaceutically acceptable salt in an amount suitable for administering in a dose ranging from 10 to 300 mg/day; and/or the angiotensin II receptor blocker in an amount suitable for administering in a dose ranging from 5 to 320 mg/day.

Advantageous Effects of Invention

It is newly found by the present invention that co-administration of the compound of Formula 1 and an angiotensin II receptor blocker such as olmesartan, olmesartan medoxomil, telmisartan, losartan, valsartan, etc. can remarkably inhibit the concentration of triglycerides in the blood; and increase HDL cholesterols in the blood, in comparison with the administration of the compound of Formula 1 alone. Therefore, the pharmaceutical composition of the present invention can be usefully applied for preventing or treating hyperlipidemia, including hypertriglyceridemia (inclusive of hypertriglyceridemia-associated diseases), hypercholesterolemia, and combined hyperlipidemia.

BEST MODE FOR CARRYING OUT THE INVENTION

The present invention provides a pharmaceutical composition for preventing or treating hyperlipidemia comprising a compound of Formula 1 or its pharmaceutically acceptable salt; and an angiotensin II receptor blocker as active ingredients:

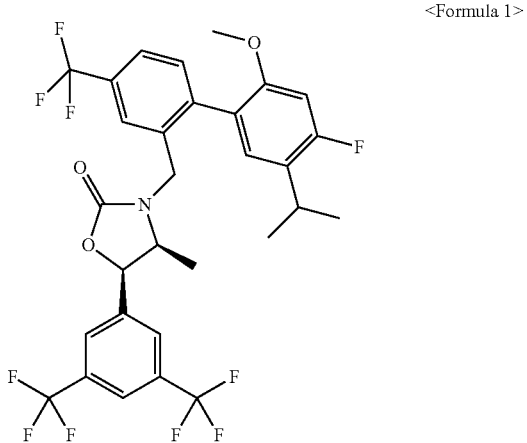 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

<Formula 1>

The compound of Formula 1 or its pharmaceutically acceptable salt may be prepared according to the disclosures in the International Publication No. WO 2006/014357. The International Publication No. WO 2006/014357 is incorporated into the present specification as a reference.

The angiotensin II receptor blocker (ARB) includes olmesartan or its salt, olmesartan medoxomil or its salt, telmisartan or its salt (e.g., sodium salt, etc.), losartan or its salt (e.g., potassium salt, etc.), and valsartan or its salt (e.g., sodium salt, calcium salt, etc.). The angiotensin II receptor blocker may be preferably olmesartan medoxomil or its salt.

In an embodiment, the pharmaceutical composition of the present invention may be a pharmaceutical composition for preventing or treating hypertriglyceridemia or hypertriglyceridemia-associated disease. The hypertriglyceridemia-associated disease refers to a disease originated from abnormally elevated level of the triglycerides in the blood. The hypertriglyceridemia-associated disease includes atherosclerosis and pancreatitis, but not limited thereto. Preferable example of the hypertriglyceridemia-associated disease includes atherosclerosis.

In another embodiment, the pharmaceutical composition of the present invention may be a pharmaceutical composition for preventing or treating hypercholesterolemia.

In still another embodiment, the pharmaceutical composition of the present invention may be a pharmaceutical composition for preventing or treating combined hyperlipidemia.

The pharmaceutical composition of the present invention may be formulated into oral or parenteral dosage forms, preferably into a dosage form for oral administration. And also, the pharmaceutical composition of the present invention may have a form obtained by formulating the compound of Formula 1 and an angiotensin II receptor blocker into a single unit dosage form. Alternatively, the pharmaceutical composition of the present invention may have a form obtained by formulating the compound of Formula 1 and an angiotensin II receptor blocker into separate dosage forms and then packaging the resulting dosage forms in a single package unit.

The pharmaceutical composition for oral administration having one or two unit dosage form(s) may include a pharmaceutically acceptable carrier, for example, diluents, disintegrating agents, sweeteners, lubricants, and/or flavoring agents, and can be formulated according to conventional methods into tablets, capsules, powders, granules, suspensions, emulsions, syrups, etc. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient(s) may be combined with emulsifying and/or suspending agents. If desired, certain sweetening and/or flavoring agents may be used. For the pharmaceutical composition for parenteral administration (for example, intramuscular, intraperitoneal, subcutaneous and intravenous administration) having one or two unit dosage form(s), sterile solutions of the active ingredient are usually prepared, and the pH of the solutions should be suitably adjusted and buffered with an isotonic agent and/or a buffering agent.

The compound of Formula 1 or its pharmaceutically acceptable salt contained in the pharmaceutical composition of the present invention may be administered in a therapeutically effective amount ranging from about 10 mg per day to about 300 mg per day to a subject patient. And also, the an angiotensin II receptor blocker may be administered in a therapeutically effective amount ranging from about 5 mg per day to about 320 mg per day to a subject patient. Of course, the dosages may be changed according to the patient's age, weight, susceptibility, symptom, etc. In an embodiment, the pharmaceutical composition of the present invention may be formulated into a dosage form for oral administration. The dosage form for oral administration may comprise the compound of Formula 1 or its pharmaceutically acceptable salt in an amount suitable for administering in a dose ranging from 10 to 300 mg/day; and/or the angiotensin II receptor blocker in an amount suitable for administering in a dose ranging from 5 to 320 mg/day. Of course, the daily dose of the angiotensin II receptor blocker depends on the kinds thereof.

The present invention also provides a use of active ingredients comprising the compound of Formula 1 (i.e., (4S,5R)-5-[3,5-bis(trifluoromethyl)phenyl]-3-({2-[4-fluoro-2-methoxy-5-(propan-2-yl) phenyl]-5-(trifluoromethyl)phenyl}methyl)-4-methyl-1,3-oxazolidin-2-one) or its pharmaceutically acceptable salt; and an angiotensin II receptor blocker for the manufacture of a medicament for preventing or treating hyperlipidemia. In the use of the present invention, the hyperlipidemia may be hypertriglyceridemia or hypertriglyceridemia-associated disease. The hypertriglyceridemia-associated disease includes atherosclerosis and pancreatitis, but not limited thereto. Preferable example of the hypertriglyceridemia-associated disease includes atherosclerosis. And also, in the use of the present invention, the hyperlipidemia may be hypercholesterolemia or combined hyperlipidemia.

The present invention comprises, within its scope, a method for treating hyperlipidemia in a patient, which comprises administering a therapeutically effective amount of the compound of Formula 1 (i.e., (4S,5R)-5-[3,5-bis(trifluoromethyl)phenyl]-3-({2-[4-fluoro-2-methoxy-5-(propan-2-yl) phenyl]-5-(trifluoromethyl)phenyl}methyl)-4-methyl-1,3-oxazolidin-2-one) or its pharmaceutically acceptable salt; and a therapeutically effective amount of an angiotensin II receptor blocker to the patient in need thereof. In the method for treating hyperlipidemia of the present invention, the hyperlipidemia may be hypertriglyceridemia or hypertriglyceridemia-associated disease. The hypertriglyceridemia-associated disease includes atherosclerosis and pancreatitis, but not limited thereto. Preferable example of the hypertriglyceridemia-associated disease includes atherosclerosis. And also, in the method for treating hyperlipidemia of the present invention, the hyperlipidemia may be hypercholesterolemia or combined hyperlipidemia.

The present invention will be described in further detail with reference to the following examples. These examples are for illustrative purposes only and are not intended to limit the scope of the present invention.

Example 1. Evaluation of Triglyceride-Inhibitory Activities in Hypercholesterolemia-Induced Animals (1) Test Method Male New Zealand White rabbits were used as a test animal. All animals, except for the G1 group animals (negative control group, n=4), were fed with an irradiation-sterilized hypercholesterolemia diet, i.e., DYET #620007 (Purina #5321 chow with 1% cholesterol, Dyets, Inc., Bethlehem, Pa. 18017), which was purchased from Central Lab. Animal Inc. In order to induce hypercholesterolemia, the animals were supplied with the diet for more than 8 weeks. After collecting the blood samples from the animals, serum biochemical analyses were performed thereon. Animals having total cholesterol levels of approximately 870 mg/dL were selected as a hypercholesterolemia-induced animal. The test materials were dissolved in saline containing 0.5% carboxymethylcellulose sodium and 1% Tween 80 and then administered directly into the stomach using an oral syringe adapted with a latex catheter, once per day for 4 weeks. The test groups are as in the following Table 1.

TABLE 1

| Group | Animal (numbers) | Dose volume (mL/kg/day) | Test material First material | Second material | Dose (mg/kg/day) First material | Second material |
|---|---|---|---|---|---|---|
| G1 | 4 | 2 | — | — | 0 | 0 |
| G2 | 8 | 2 | — | — | 0 | 0 |
| G3 | 8 | 2 | Compound of Formula 1 | — | 20 | 0 |
| G4 | 8 | 2 | Compound of Formula 1 | Olmesartan medoxomil | 20 | 3 |
| G5 | 8 | 2 | Compound of Formula 1 | Telmisartan | 20 | 5 |
| G6 | 8 | 2 | Compound of Formula 1 | Losartan | 20 | 10 |
| G7 | 8 | 2 | Compound of Formula 1 | Valsartan | 20 | 10 |

The blood samples were collected through the jugular vein, from the animals at the day initiating the hypercholesterolemia diet supply (i.e., before feeding), and from the animals (which were fasted for 12 to 16 hours before collecting the blood) at 2 weeks and at 4 weeks after initiating the administration of the test material(s).

(2) Results

The triglyceride concentrations in the hypercholesterolemia-induced animals as in the above are presented in the following Table 2. The values in Table 2 represent average triglyceride concentrations (mg/dL) of the respective group.

TABLE 2

| Group | 0 week | 2 weeks | 4 weeks |
|---|---|---|---|
| G1 | 66.3 | 99.5 | 52.5 |
| G2 | 192.6 | 315.1 | 544.1 |
| G3 | 167.4 | 255.8 | 356.7 |
| G4 | 122.0 | 156.6 | 145.6 |
| G5 | 188.7 | 123.7 | 111.2 |
| G6 | 86.2 | 112.8 | 114.3 |
| G7 | 131.4 | 138.4 | 135.0 |

As shown in Table 2, when the compound of Formula 1 and/or the angiotensin II receptor blockers were orally administered repeatedly for 4 weeks, the co-administration groups (G4 to G7) showed remarkably high triglyceride-inhibitory activities, in comparison with the group administered with the compound of Formula 1 alone (G3, 356.7 mg/dL at the 4 weeks after initiating the administration). Especially, the co-administration group of the compound of Formula 1 and telmisartan (G5) showed the most potent triglyceride-inhibitory activity. Therefore, it is expected that the combination of the compound of Formula 1 and the angiotensin II receptor blocker such as olmesartan, olmesartan medoxomil, telmisartan, losartan, or valsartan can be usefully applied for preventing or treating hypertriglyceridemia or hypertriglyceridemia-associated diseases.

Example 2. Evaluation of Activities in Hypertriglyceridemia and Hypercholesterolemia-Induced Animals (1) Test Method Male New Zealand White rabbits were used as a test animal. All animals, except for the G1 group animals (negative control group), were fed with an irradiation-sterilized hypertriglyceridemia and hypercholesterolemia diet, i.e., DYET #621082 (Purina #5321 chow with 0.5% cholesterol, 14% coconut oil & 2% Maltose Dextrin, Dyets, Inc., Bethlehem, Pa. 18017), which was purchased from Saeronbio Inc. In order to induce hypertriglyceridemia and hypercholesterolemia, the animals were supplied with the diet for more than 4 weeks. After collecting the blood samples from the animals, serum biochemical analyses were performed thereon. Animals showing significant changes in total cholesterol levels and triglyceride levels were selected, in comparison with the non-treated control group. The selected animals were divided into 4 groups on the basis of the total cholesterol levels and triglyceride levels, thereby all the groups having substantially equal average values in the total cholesterol levels and triglyceride levels. The test materials were dissolved in saline containing 0.5% carboxymethylcellulose sodium and 1% Tween 80 and then administered directly into the stomach using an oral syringe adapted with a latex catheter, once per day for 4 weeks. The test groups are as in the following Table 3.

TABLE 3

| Group | Dose volume (mL/kg/day) | Test material First material | Second material | Dose (mg/kg/day) First material | Second material |
|---|---|---|---|---|---|
| G1 | 2 | — | — | 0 | 0 |
| G2 | 2 | — | — | 0 | 0 |
| G3 | 2 | Compound of Formula 1 | — | 20 | 0 |
| G4 | 2 | — | Olmesartan medoxomil | 0 | 3 |
| G5 | 2 | Compound of Formula 1 | Olmesartan medoxomil | 20 | 3 |

The blood samples were collected through the jugular vein, from the animals at the day initiating the administration of the test material(s) (i.e., at the time of group-dividing, 0 week), and from the animals (which were fasted for 12 to 16 hours before collecting the blood) at 4 weeks after initiating the administration of the test material(s) (n=4-7).

(2) Results

The triglyceride concentrations in the hypertriglyceridemia and hypercholesterolemia-induced animals as in the above are presented in the following Table 4. The values in Table 4 represent average triglyceride concentrations (mg/dL) of the respective group.

TABLE 4

| Group | 4 weeks | Percent inhibition of triglyceride in the blood (%) |
|---|---|---|
| G1 | 35.7 | — |
| G2 | 326.5 | — |
| G3 | 293.1 | 10.2 |
| G4 | 217.4 | 33.4 |
| G5 | 139.4 | 57.3 |

As shown in Table 4, when the compound of Formula 1 and/or olmesartan medoxomil were orally administered repeatedly for 4 weeks, the groups administered with the compound of Formula 1 alone (G3) or olmesartan medoxomil alone (G4) respectively showed 10.2% and 33.4% inhibitions in the triglyceride levels, in comparison with the G2 group. However, the co-administration groups (G5) showed 57.3% inhibition in the triglyceride level in comparison with the G2 group. The triglyceride-inhibitory activity (i.e., 57.3% inhibition) of G5 was more potent in comparison with the sum of triglyceride-inhibitory activities of G3 and G4 (i.e., 43.6% inhibition). Therefore, it can be acknowledged that the combination of the compound of Formula 1 and the angiotensin II receptor blocker such as olmesartan medoxomil provides potent synergistic effect in inhibiting triglyceride levels.

The HDL cholesterol concentrations in the blood samples are presented in the following Table 5. The values in Table 5 represent average HDL cholesterol concentrations (mg/dL) measured from the blood sample of the respective group.

TABLE 5

| Groups | 4 weeks | Percent increase of HDL cholesterol level (%) |
|---|---|---|
| G1 | 8.1 | — |
| G2 | 122.2 | — |
| G3 | 168.5 | 37.9 |
| G4 | 125.3 | 2.6 |
| G5 | 193.9 | 58.7 |

As shown in Table 5, when the compound of Formula 1 and/or olmesartan medoxomil were orally administered repeatedly for 4 weeks, the groups administered with the compound of Formula 1 alone (G3) or olmesartan medoxomil alone (G4) respectively showed 37.9% and 2.6% increases in the blood HDL cholesterol levels, in comparison with the G2 group. However, the co-administration groups (G5) showed 58.7% increase in the blood HDL cholesterol level in comparison with the G2 group; and showed potent synergistic effect in comparison with the respective G3 and G4 groups. Therefore, it is expected that the combination of the compound of Formula 1 and the angiotensin II receptor blocker such as olmesartan medoxomil can be usefully applied for preventing or treating hypercholesterolemia and combined hyperlipidemia, as well as hypertriglyceridemia (including hypertriglyceridemia-associated diseases).

The invention claimed is:

1. A method for treating hypertriglyceridemia, hypertriglyceridemia-associated atherosclerosis or hypertriglyceridemia-associated pancreatitis in a patient, which comprises administering a therapeutically effective amount of a compound of Formula 1 or its pharmaceutically acceptable salt in combination with a therapeutically effective amount of olmesartan medoxomil or its pharmaceutically acceptable salt to the patient in need thereof, wherein the combination is synergistic in treating the hypertriglyceridemia, hypertriglyceridemia-associated atherosclerosis or hypertriglyceridemia-associated pancreatitis, and the compound of Formula 1 or its pharmaceutically acceptable salt is administered in a dose of 20 mg/kg/day and the olmesartan medoxomil or its pharmaceutically acceptable salt is administered in a dose of 3 mg/kg/day:

<Formula 1>
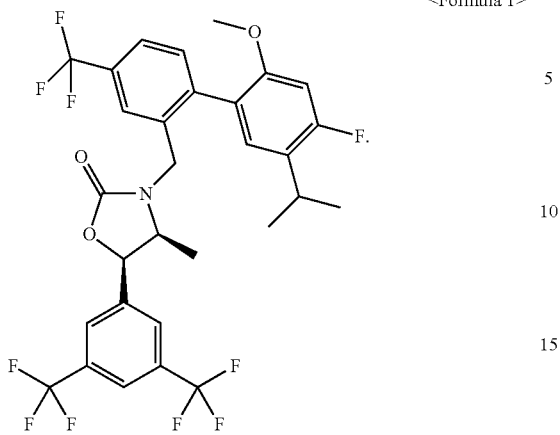
2. The method according to claim 1, wherein the administering is carried out with a dosage form for oral administration.
* * * * *